United States Patent [19]
Johnson et al.

[11] Patent Number: 5,391,181
[45] Date of Patent: Feb. 21, 1995

[54] ORTHOPAEDIC HOLDING FORCEPS

[75] Inventors: Erin M. Johnson; Mark A. Lazzeri, both of Warsaw, Ind.

[73] Assignee: Zimmer, Inc., Warsaw, Ind.

[21] Appl. No.: 141,769

[22] Filed: Oct. 22, 1993

[51] Int. Cl.6 .............................................. A61B 17/00
[52] U.S. Cl. ................... 606/207; 81/424.5
[58] Field of Search .................. 606/205–211, 606/72, 73, 96, 104, 53, 107, 108; 81/424.5, 426.5; 128/898; 294/99.2

[56] References Cited

U.S. PATENT DOCUMENTS

| | | |
|---|---|---|
| 2,387,928 | 10/1945 | Monnier ........................ 81/426.5 |
| 2,570,465 | 10/1951 | Lundholm . |
| 2,842,997 | 7/1958 | Wentling . |
| 4,140,111 | 2/1979 | Morrill . |
| 4,776,328 | 10/1988 | Frey et al. . |
| 4,858,601 | 8/1989 | Glisson . |
| 4,887,612 | 12/1989 | Esser et al. ...................... 606/208 |
| 4,901,712 | 2/1990 | Voegell et al. . |
| 4,903,691 | 2/1990 | Heinl . |
| 4,903,692 | 2/1990 | Reese . |
| 4,911,154 | 3/1990 | Vickers . |
| 4,963,144 | 10/1990 | Huene . |
| 4,995,810 | 2/1991 | Soderberg . |
| 5,019,080 | 5/1991 | Hemer . |

OTHER PUBLICATIONS

Zimmer, Inc.—Catalog pp. A87, A97, A99—Acetabular Components—Screwdriver and Screw Holding Instruments—1991.

Zimmer, Inc.—Catalog pp. D39, D40, C53, C54, E60, E61, E62—Various Screw and Screwdriver Instruments—1987.

*Primary Examiner*—Stephen C. Pellegrino
*Assistant Examiner*—William W. Lewis
*Attorney, Agent, or Firm*—Margaret L. Geringer

[57] ABSTRACT

An orthopaedic holding forceps 1 for simultaneously holding a screw 60 and a screwdriver 70. The forceps 1 includes a distal tip 42 having an upper chamber 43 adapted for receiving an enlarged gripping head 72 of the screwdriver 70 and a lower chamber 44 adapted for receiving the enlarged head 61 of screw 60. The distal tip 42 also includes an interconnecting chamber 45 between the upper and lower chambers 43 and 44 adapted for receiving the distal driving tip 73 of the screwdriver 70.

9 Claims, 2 Drawing Sheets

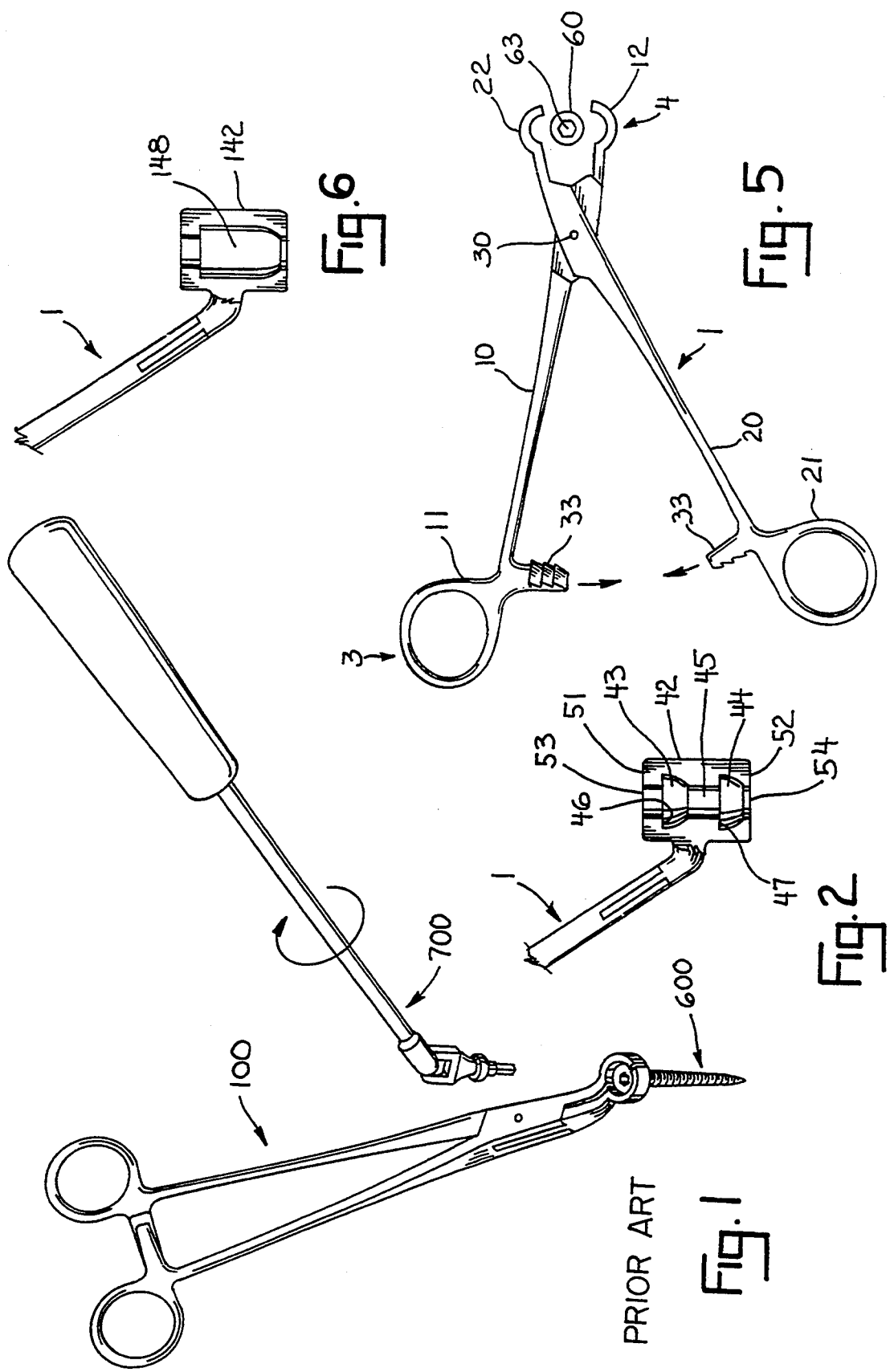

ORTHOPAEDIC HOLDING FORCEPS

BACKGROUND OF THE INVENTION

The present invention relates to an orthopaedic holding forceps. In particular, this invention relates to such a forceps for simultaneously holding and gripping both a surgical screw and screwdriver during a surgical procedure.

It is known in the art to grip screws with instruments or to stabilize a screwdriver during a surgical procedure. For example, as shown in the prior art device of FIG. 1 a forceps 100 grips an enlarged head of a screw 600 in the single chamber of the forceps while a screwdriver 700 is applied from the exterior of the forceps to the exposed recess of the screw to turn it into a desired location, such as into a bone or into an implant with screw holes therein. Then when the head is released from the forceps, so that it can be fully seated, the single chamber of the forceps can be used to grip an enlarged gripping head on the screwdriver. The screwdriver can then be turned to turn the screw and fully seat the screw.

SUMMARY OF THE INVENTION

The present invention provides an orthopaedic holding forceps for simultaneously holding a screw and a screwdriver. The forceps includes a distal tip having an upper chamber adapted for receiving an enlarged gripping head of the screwdriver and a lower chamber adapted for receiving the enlarged head of the screw. The distal tip also includes an interconnecting chamber between the upper and lower chambers adapted for receiving the distal driving tip of the screwdriver.

Accordingly, it is an advantage of the invention to provide a novel instrument which provides a positive means for simultaneously holding the enlarged head of a screw and the enlarged gripping portion of the screwdriver.

Another advantage of the invention is to provide more control during a surgical procedure by controlling the positioning of both the screw and screwdriver.

A further advantage of the invention is to provide an instrument which is able to maintain the screwdriver driving tip in the recess of the screw, so that it is not able to slip out of the screw head while both of the screw and screwdriver are simultaneously positioned in the forceps.

A still further advantage of the invention is the ability to maintain the screw on the screwdriver without having to separately control the screwdriver in order to keep it securely in contact with the screw head.

Still other advantages of the invention will become apparent upon reference to the accompanying drawings.

BRIEF DESCRIPTION OF THE DRAWINGS

FIG. 1 is a perspective view of a prior art holding forceps gripping a screw, with a screwdriver positioned exteriorly of the forceps.

FIG. 2 is a partial side view of an orthopaedic holding forceps in accordance with the present invention with one of the jaw halves of the distal tip broken away.

FIG. 5 is a top view of the instrument of FIG. 2 shown in an opened position, with a screw position in the space between the jaw halves of the instrument.

FIG. 6 is a partial side view of an alternate embodiment of the distal tip of the forceps with one of the jaw halves broken away.

DESCRIPTION OF THE PREFERRED EMBODIMENT

The preferred embodiment described herein is not intended to be exhaustive or to limit the invention to the precise form disclosed. Rather, it is chosen and described to best explain the invention so that others skilled in the art might utilize its teachings.

Figure 4:
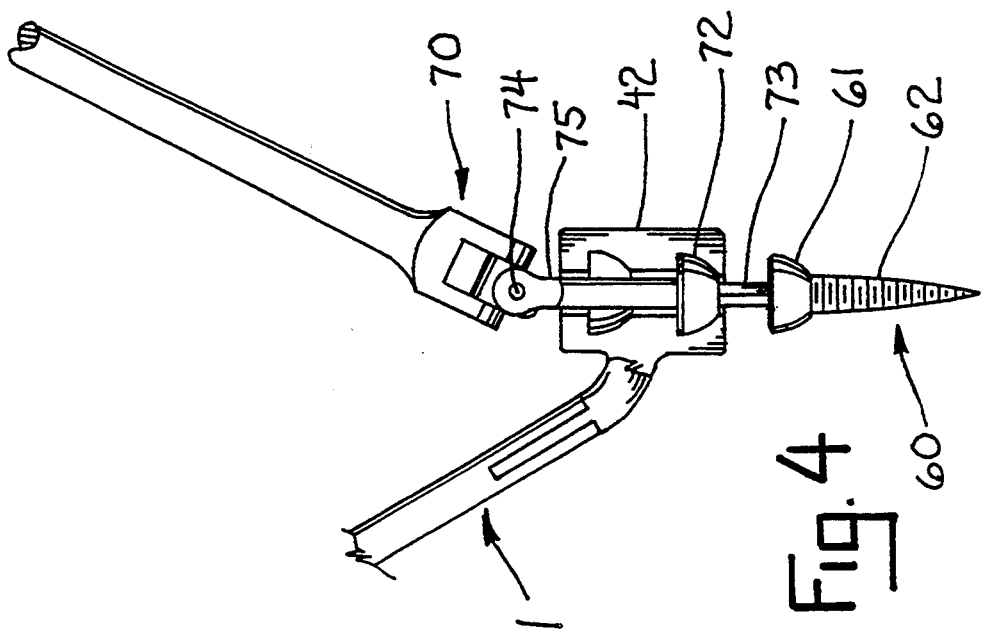
FIG. 4 is a partial side view of the instrument of FIG. 2 with one of the jaw halves broken away, shown with only the screwdriver secured thereto.
Figure 3:
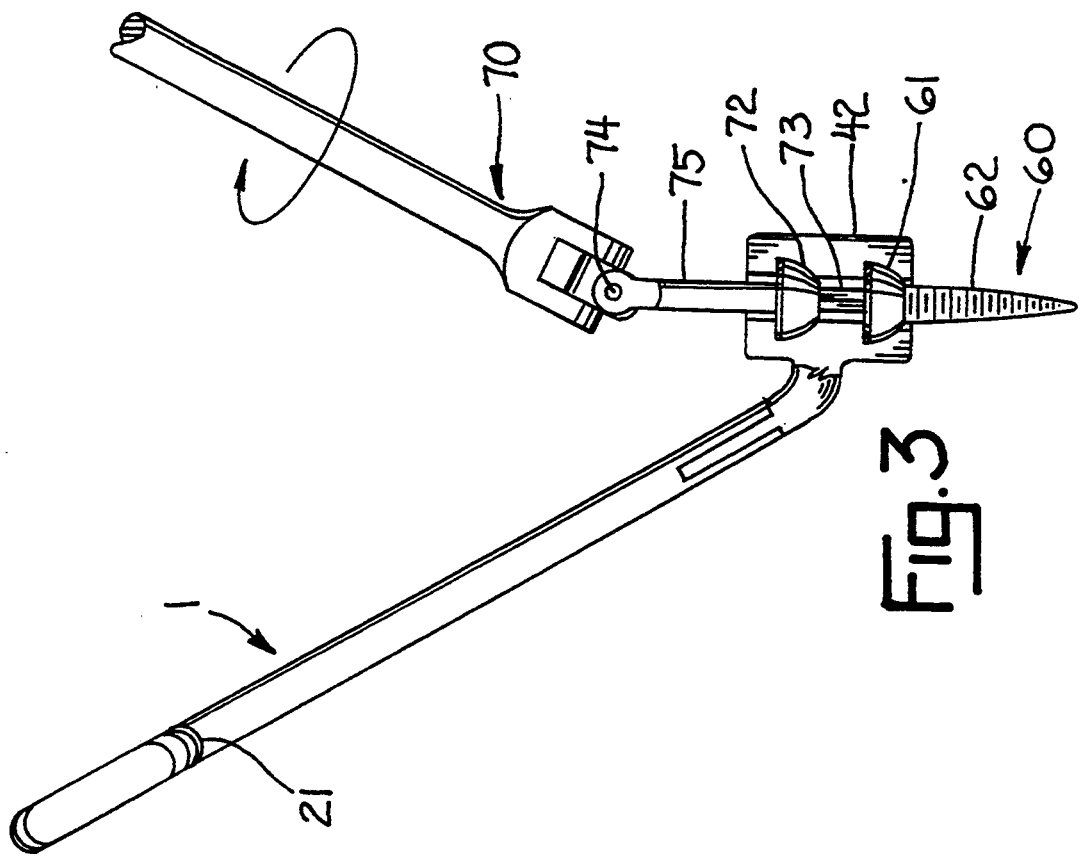
FIG. 3 is a side view of the instrument of FIG. 2 with one of the jaw halves broken away, shown with a screw and screwdriver secured thereto.

Accordingly, FIGS. 2-5 illustrate the preferred embodiment of an orthopaedic holding forceps 1 in accordance with the present invention. This invention relates to such a forceps 1 for simultaneously holding therein a surgical screw 60 having an enlarged head 61 with a driving recess 63 therein and a shaft 62 extending therefrom, and holding a screwdriver 70 having an enlarged gripping head 72 with a distal driving tip 73 extending therefrom. The forceps 1 includes a distal tip 42 having an upper chamber 43 adapted for receiving the enlarged gripping head 72 of screwdriver 70 and a lower chamber 44 adapted for receiving the head 61 of screw 60 and an interconnecting chamber 45 therebetween adapted for receiving the driving tip 73 of screwdriver 70. The driving recess 63 and driving tip 73 may be any suitable corresponding shapes, such as hex-shaped or any other suitable mating shapes for driving interconnection.

The upper and lower chambers 43 and 44 are preferably each enlarged, with the interconnecting chamber 45 being narrower than the enlarged upper and lower chambers 43 and 44. This enables the forceps 1 to more securely grip the enlarged screw head 61 and the enlarged gripping head 72 of the screwdriver 70.

The distal tip 42 of forceps 1 includes a top surface 51 and a bottom surface 52. The top surface includes a top opening 53 therein extending into upper chamber 43. Bottom surface 52 includes a bottom opening 54 therein extending into bottom chamber 44. The enlarged upper chamber 43 has a shape which preferably corresponds to the shape of the enlarged gripping head 72 of screwdriver 70, and the enlarged lower chamber 44 has a shape which preferably corresponds to the shape of the enlarged head 61 of screw 60. The enlarged upper and lower chambers each have an upper retaining surface 46 and 47, respectively, to help maintain the relative positioning of the item secured therein. The enlarged upper and lower chambers 43 and 44 retain the screwdriver 70 and screw 60, but are large enough to allow rotational movement of the screwdriver and screw therein.

The enlarged upper and lower chambers 43 and 44 preferably have substantially the same shape, so that either the head 61 of the screw 60 or the enlarged gripping head 72 could be accommodated therein as desired during the surgical procedure, making the forceps 1 more adaptable.

The forceps 1 includes first and second intersecting arms 10 and 20 interconnected by a pivot pin 30. The distal tip 42 is comprised of a first jaw half 12 at a distal end 4 of the first arm 10 and a second jaw half 22 and a distal end 4 of the second arm 20. The first and second arms 10 and 20 can be pivoted to open and spread the first and second jaw halves 12 and 22 apart or pivoted to close the first and second jaw halves 12 and 22 together for gripping and holding the screw 60 and screwdriver 70. The arms 10 and 20 may include serrated locking extensions 33 extending from each arm 10 and 20 to selectively secure the relative position of arms 10 and 20. It is well known in the art to provide such locking extensions 33. Each arm 10 and 20 may suitably include a handle 11 and 21 at a proximal end 3 of forceps 1. It is further noted that while the forceps 1 may be suitably made of stainless steel, any suitable materials and manufacturing methods may be utilized.

The screwdriver 70 may include a pivot 74 to enable the screwdriver position to be varied relative to the distal tip 73, such as is known in the art (as also shown by prior art screwdriver 700). Screwdriver 70 may be similar to the prior art screwdriver 700 shown in FIG. 1 except that the portion 75 directly above the enlarged gripping head 72 is preferably much longer in order to be adapted for use with the forceps 1 of the present invention to enable the gripping head 72 to be positioned in either the upper or lower chamber 43 or 44 as described by the preferred method of use below.

The forceps 1 is opened to spread the first and second jaw halves 12 and 22 apart. The head 61 of screw 60 is positioned in one of the jaw halves of lower chamber 44 of forceps 1, and the gripping head 72 of screwdriver 70 is positioned in a corresponding jaw half of upper chamber 43 of forceps 1, such that the driving tip 73 is in the interconnecting chamber of a corresponding jaw half, so that the driving tip 73 extends into operative engagement with recess 63 in head 61 of screw 60. The first and second jaws are then closed to simultaneously grip and hold the screw 60 and screwdriver 70 in forceps 1. The forceps 1 may be locked in the closed position via serrated locking extensions 33.

The screw 60 is then positioned or held in a desired location, such as against the bone or through a screw hole in an implant, such as an acetabular cup with screw holes (not shown). The screwdriver 70 is turned to turn the screw to insert the screw 60, while controlling both the screw 60 and screwdriver 70 with holding forceps 1. After the shaft 62 has been substantially inserted, the forceps 1 is then opened or unlocked. The forceps 1 is removed from the screw 60 and screwdriver 70. The gripping head 72 of screwdriver 70 is then. repositioned in one of the jaw halves of the lower chamber 44, while screw 60 is no longer captured by forceps 1. The first and second jaw halves are then closed about gripping head 72 to hold screwdriver 70. The screwdriver 70 is then again turned with driving tip 73 positioned in recess 63 of screw 60 to continue insertion of screw 60 and ultimately to fully seat the head of the screw 60 and complete insertion thereof.

It is noted that FIG. 6 illustrates an alternate embodiment for the distal tip 142 which can still accommodate both the screw head 61 and enlarged gripping head 72 and distal driving tip 73 of screwdriver 70 therein due to the elongated length of chamber 148 which does not provide for the discrete separation between the chambers as in the embodiment of FIG. 2.

While this invention has been described in terms of a particularly advantageous embodiment, those skilled in the art can appreciate that modifications can be made without departing from the spirit and scope of the invention.

We claim:

1. An orthopaedic holding forceps for simultaneously holding therein a surgical screw having an enlarged head with a driving recess therein and a shaft extending therefrom and holding a screwdriver having an enlarged gripping head with a distal driving tip extending therefrom, wherein the forceps includes a distal tip having an upper chamber adapted for receiving the enlarged gripping head of the screwdriver and a lower chamber adapted for receiving the head of the screw and an interconnecting chamber therebetween adapted for receiving the driving tip of the screwdriver, and wherein the distal tip includes a top surface and a bottom surface and wherein the top surface includes a top opening therein extending into the upper chamber and the bottom surface includes a bottom opening therein extending into the bottom chamber, and wherein the width of the top opening is narrower than the upper chamber to form a first upper retaining surface and the width of the bottom opening is narrower than the bottom chamber to simultaneously retain the head of the surgical screw and the enlarged gripping head of the screwdriver securely therein.

2. The forceps of claim 1 wherein the upper and lower chambers are each enlarged and the interconnecting chamber is narrower than the enlarged upper and lower chambers.

3. The forceps of claim 2 wherein the enlarged upper chamber has a shape which corresponds to the shape of the enlarged gripping head of the screwdriver and the enlarged lower chamber has a shape which corresponds to the shape of the enlarged head of the screw and wherein the enlarged lower chamber includes a second upper retaining surface.

4. The forceps of claim 3 wherein the enlarged upper and lower chambers are substantially the same shape.

5. The forceps of claim 1 wherein the forceps includes first and second intersecting arms interconnected by a pivot pin and wherein the distal tip is comprised of a first jaw half at a distal end of the first arm and a second jaw half at a distal end of the second arm and wherein the first and second arms can be pivoted to open and spread the first and second jaw halves apart or pivoted to close the first and second jaw halves together for gripping and holding the screw and screwdriver.

6. A method of using an orthopaedic holding forceps for holding therein a bone screw having an enlarged head with a driving recess therein and a shaft extending therefrom and holding a screwdriver having an enlarged gripping head with a distal driving tip extending therefrom, wherein the forceps includes a distal tip having an upper chamber and a lower chamber and an interconnecting chamber therebetween, and wherein the forceps includes first and second intersecting arms interconnected by a pivot pin and wherein the distal tip is comprised of a first jaw half at a distal end of the first arm and a second jaw half at a distal end of the second arm and wherein the first and second arms can be pivoted to open and spread the first and second jaw halves apart or pivoted to close the first and second jaw halves together, wherein the method includes the following steps:

a) opening the forceps to spread the first and second jaw halves apart;

b) positioning the head of the screw in the lower chamber of the forceps;

c) positioning the gripping head of the screwdriver in the upper chamber of the forceps and the driving tip in the interconnecting chamber, so that the driving tip extends into operative engagement with the recess in the head of the screw; and d) closing the first and second jaw halves to simultaneously grip and hold the screw and screwdriver in the forceps.

7. The method of claim 6 wherein the method further includes the following:

a) positioning the screw in a desired location and turning the screwdriver to insert the screw while controlling both the screw and screwdriver with the holding forceps;

b) opening the forceps;

c) removing the forceps from the screw and screwdriver;

d) repositioning the gripping head of the screwdriver in the lower chamber, while the screw is no longer captured by the forceps;

e) closing the first and second jaw halves about the gripping head to hold the screwdriver; and f) turning the screwdriver with the driving tip positioned in the recess of the screw head to continue insertion of the screw.

8. A method of using an orthopaedic holding forceps for holding therein a bone screw having an enlarged head with a driving recess therein and a shaft extending therefrom and holding a screwdriver having an enlarged gripping head with a distal driving tip extending therefrom, wherein the forceps includes a distal tip having an elongated chamber means for simultaneously retaining the enlarged gripping head of the screwdriver and the head of the surgical screw, and wherein the forceps includes first and second intersecting arms interconnected by a pivot pin and wherein the distal tip is comprised of a first jaw half at a distal end of the first arm and a second jaw half at a distal end of the second arm and wherein the first and second arms can be pivoted to open and spread the first and second jaw halves apart or pivoted to close the first and second jaw halves together, wherein the method includes the following steps:

a) opening the forceps to spread the first and second jaw halves apart;

b) positioning the head of the screw in a lower portion of the chamber means of the forceps;

c) positioning the gripping head of the screwdriver in an upper portion of the chamber means of the forceps so that the driving tip extends into operative engagement with the recess in the head of the screw; and d) closing the first and second jaw halves to simultaneously grip and hold the screw and screwdriver in the forceps.

9. The method of claim 8 wherein the method further includes the following:

a) positioning the screw in a desired location and turning the screwdriver to insert the screw while controlling both the screw and screwdriver with the holding forceps;

b) opening the forceps;

c) removing the forceps from the screw and screwdriver;

d) repositioning the gripping head of the screwdriver in the lower portion of the chamber means, while the screw is no longer captured by the forceps;

e) closing the first and second jaw halves about the gripping head to hold the screwdriver; and f) turning the screwdriver with the driving tip positioned in the recess of the screw head to continue insertion of the screw.

* * * * *